United States Patent [19]

Kohara et al.

[11] Patent Number: 4,512,870

[45] Date of Patent: Apr. 23, 1985

[54] CHEMICALLY SENSITIVE ELEMENT

[75] Inventors: Satsuki Kohara, Koganei; Noriaki Ono, Akishima, both of Japan

[73] Assignee: Olympus Optical Co., Ltd., Japan

[21] Appl. No.: 557,610

[22] Filed: Dec. 2, 1983

[30] Foreign Application Priority Data

Dec. 6, 1982 [JP] Japan .................................. 57-213693

[51] Int. Cl.³ .............................................. G01N 27/30
[52] U.S. Cl. .................................. 204/416; 204/418; 204/419; 357/25
[58] Field of Search ............... 204/416, 418, 419, 420; 357/25; 324/71.5; 128/635

[56] References Cited

U.S. PATENT DOCUMENTS

| | | | |
|---|---|---|---|
| 3,719,564 | 3/1973 | Lilly et al. | 204/1 T |
| 3,831,432 | 8/1974 | Cox | 73/23 |
| 4,020,830 | 5/1977 | Johnson | 128/635 |
| 4,273,636 | 6/1981 | Shimada et al. | 204/419 X |
| 4,411,741 | 10/1983 | Janata | 204/1 T |

OTHER PUBLICATIONS

12th Conference of the Medical Engineering Society of Japan, Copendium of Scheduled Addresses, May 1973.
Documentary Materials for Research Meeting on Electrical Measurement—Documents No. EM-74-22 through 31, "New Fields of Instrumentation v. Bio--Electrical Instrumentation, Jan. 28, 29, 1974, Japan.

Moody et al, "Selective Ion Sensitive Electrodes", Merrow Technical Library, 1971.
Fiedler et al, "Selectrode—The Universal Ion-Selective Electrode", Part VII. A Valinomycin–Based Potassium Electrode with Nonporous Polymer Membrane and Solid-State Inner Reference System, Analytica Chimica Acta. 67, (1973), 179-193.
Gough et al, "Enzyme Electrodes", Science, vol. 180, pp. 380-384.
Bergveld, "Development, Operation and Application of the Ion–Sensitive Field-Effect Transistor as a Tool for Electrophysiology", IEEE Transactions on Biomedical Engineering, vol. BME-19, No. 5, Sep. 1972.

Primary Examiner—G. L. Kaplan
Attorney, Agent, or Firm—Ostrolenk, Faber, Gerb & Soffen

[57] ABSTRACT

A chemical sensing element suitable for measurement of the activity or the concentration of a specific ion contained in an electrolyte is provided with an optically opaque membrane between a gate insulating membrane and an ion sensing membrane of a field-effect type transistor. Since the opaque membrane is provided, extraneous light impinging on a gate is blocked by the opaque membrane, whereby an erroneous potential due to extraneous light is prevented. Accordingly, the accurate measurement of the activity or the concentration of a specific ion contained in an electrolyte may be achieved even in intense ambient light.

4 Claims, 4 Drawing Figures

4,512,870

CHEMICALLY SENSITIVE ELEMENT

BACKGROUND OF THE INVENTION

The present invention relates to a chemically sensitive element, and more particularly, to such an element which may be used to determine the activity or the concentration of a specified ion contained in an electrolyte.

There has been proposed a chemically sensitive element for determining the activity or the concentration of a specific ion contained in an electrolyte, which element has the construction of the field-effect transistor type as shown in FIG. 1, which is also known as an ion sensor. The ion sensor 11 of the field-effect transistor (hereinafter abbreviated as ISFET), which is oblong as viewed in a plane, comprises a gate 12, which has an ion sensing portion at the right end of FIG. 1, a lead portion 13 for a source and a lead portion 14 for a drain at the middle of the left side of FIG. 1.

In a section view of the gate 12, taken on section line II—II in FIG. 2, its configuration is long sideways hexagonal in shape and there are provided an n-type drain diffusion region 26 at the middle and upper surface side of a p-type silicon substrate 22 and an n-type source diffusion region 27 at both ends thereof. The entirety of the gate is covered by a gate insulating membrane 23 and is further covered by a protecting membrane 24 such that when immersed in a solution to be examined the gate insulating membrane 23 will not swell due to the solution. In addition, an ion sensing membrane 25 is provided on the upper surface of the protecting membrane 23 by the drain and the source diffusion region 26 and 27 sides.

The ion sensing membrane 25 varies in its composition depending upon the specific ion to be sensed. By way of example, when a sensing membrane for sensing a hydrogen ion (H+) is provided, it shows a potential gradient of approximately 50 mV/pH in gate voltage.

However, when light impinges on membrane 25 the light reaches the silicon substrate 22, resulting in that an erroneous signal to the extent of 0.1 in pH, even in indoor illumination, due to the photoelectric effect within the semiconductor. Thus it is impossible to achieve an accurate measurement of the concentration of an ion.

SUMMARY OF THE INVENTION

It is an object of the present invention to provide a chemically sensing element of the field-effect transistor type in which an optically opaque membrane is provided between the gate insulating membrane and the ion sensing membrane.

According to the invention, since the optically opaque membrane is provided between the ion sensing membrane and the gate insulating membrane, extraneous light impinging on the gate of the chemically sensing element is blocked by the optically opaque membrane and an erroneous signal due to extraneous light is prevented. Accordingly, it is possible to achieve an accurate measurement of the activity or the concentration of an ion in an electrolyte even in the presence of intense light.

DESCRIPTION OF THE PREFERRED EMBODIMENTS

Figure 1:
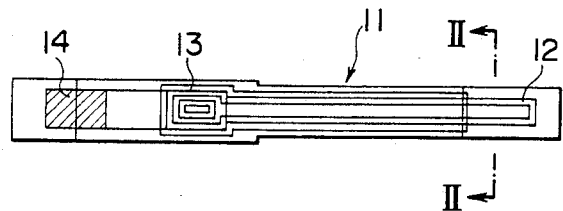
FIG. 1 is a plan view illustrating one example of chemically sensing elements heretofore in use.
Figure 2:
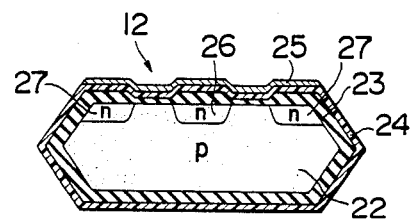
FIG. 2 is a cross-section of the chemically sensing element of FIG. 1 taken on line II—II of FIG. 1.
Figure 3:
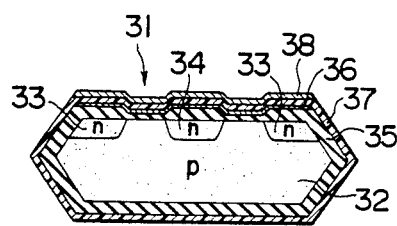
FIG. 3 is a cross-section of one embodiment of a chemically sensing element of the present invention.

Referring now to FIG. 3, an ion sensing portion 31 of a chemically sensing element according to the invention has a section of substantially long sideways hexagonal shape similar to that of the same portion of the conventional chemically sensitive element shown in FIG. 2. In the ion sensing portion 31, there are provided n-type source diffusion regions 33 at both ends of a p-type substrate 32 and an n-type drain diffusion region 34 at the middle thereof. The whole of the ion sensing portion is coated with a gate insulating membrane 35 formed of an oxide film. Additionally, an optically opaque membrane 36 is provided on the upper surface of the gate insulating membrane 35. The sides of the source and the drain diffusion region 33, 34 and the whole of these membranes is covered by a protecting membrane 37. An ion sensing membrane 38 is further provided on the upper surface of the protecting membrane 37 above the opaque membrane 36.

Any material through which light does not pass may be used as the optically opaque membrane 36. For example, adhesive chromium or tantalum is used and it may be formed by a method of vacuum evaporation, sputtering or the like. The thickness of 2000 Å or more for the opaque membrane formed of chromium or tantalum is sufficient to eliminate an erroneous potential.

As for the protecting membrane 37, which prevents permeation of ions, any film having the good insulating and water-tight properties may be used. For example, silicon nitride, silicon oxynitride, one of oxide or nitride of aluminum or tantalum, or a mixture of these compounds may be used and it may be formed by a method of CVD (chemical vapor deposition), sputtering or the like.

The ion sensing membrane 38 may be formed as an ion sensor for detecting the activity or the concentration of an ion by a film of, for example, silicon nitride ($Si_3N_4$), alumina ($Al_2O_3$), tantalum pentoxide or the like as for the detection of hydrogen ions (H+).

When a membrane approximately 1000 Å thick of silicon nitride or alumina is used as the sensing membrane 38, an interface potential from 53 to 56 mV/pH in the range from 1 to 13 in pH is obtained, which is substantially the same as that of a glass electrode heretofore in use.

These membranes 38 of inorganic materials are formed by a method of CVD, sputtering or the like.

Aluminosilicate glass ($SiO_2$—$Al_2O_3$—$Na_2O$) or the like is used as a sodium ($Na^+$) or potassium ($K^+$) sensor.

In practice, the chemically sensing element thus constructed is enclosed in a pipe of vinyl chloride or the like with only the gate (ion sensing portion) 31 exposed. The sensor is then immersed in a solution to be examined, together with a reference electrode.

In operation, when the ion sensing portion 31 is immersed in a solution to be examined, the so-called gate voltage varies in accordance with the concentration of a specific ion in the solution, and the conductivity in the channel region between the source and the drain also varies. As a result, the current between the source and the drain varies. Thus, the concentration of the specific ion in the solution can be determined by measuring the variation in the current or the conductivity by means of an external measuring circuit and thus obtaining the so-called gate voltage.

Furthermore, even when the ion sensing element is used in a bright area, extraneous light is blocked by the opaque membrane 36 and hence does not reach the ion sensing portion 31. Accordingly, the generation of a potential in the semiconductor by extraneous light is prevented and measurement of the ion concentration is independent of extraneous light.

Figure 4:
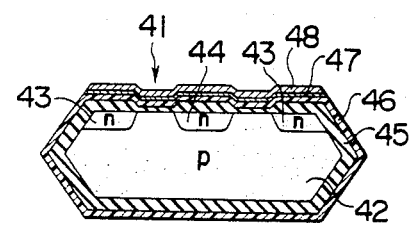
FIG. 4 is a section view of a chemically sensing element illustrating another embodiment of the invention.

In FIG. 4, which illustrates a chemically sensing element of a second embodiment according to the invention, the arrangement of a p-type substrate 42, an n-type source and an n-type drain diffusion region 43, 44 and a gate insulating membrane 45 in an ion sensing portion or a gate 41 is the same as in the first embodiment shown in FIG. 3.

While the chemically sensing element of FIG. 3 is provided with the optically opaque membrane between the gate insulating membrane 35 and the protecting membrane 37, in the second embodiment an optically opaque membrane 47 is provided between a protecting membrane 46 and an ion sensing membrane 48.

In the second embodiment, extraneous light is also blocked by the opaque membrane 47 and thus the accurate measurement of the ion concentration may be achieved independently of intensity of extraneous light.

Although in each of the first and second embodiments, the chemically sensing element including the protecting membrane is described, it should be understood that the sensing element may be sufficient for use if only an optically opaque membrane is provided between the ion sensing membrane and the gate insulating membrane, whether a protecting membrane exists or not.

In the first embodiment shown in FIG. 3, the protecting membrane and the ion sensing membrane in the ISFET, for example, for detecting a hydrogen ion, may be formed of the same material such as $Si_3N_4$, $Al_2O_3$, $Ta_2O_5$. Accordingly, when one of the above materials is used as the protecting membrane 37, there is no need to particularly provide the ion sensing membrane 38, resulting in the provision of an ISFET of a simpler construction.

Additionally, while the substrate of the p-type and the source and the drain diffusion region of the n-type are used in the foregoing description, it will be noted that polarities of the substrate and these regions may be reversed.

What is claimed is:

1. A chemically sensitive element of the ion sensing field-effect transistor type including a semiconductor substrate having source, drain and channel regions; a gate insulating membrane disposed atop said channel region; an optically opaque membrane disposed atop said gate insulating membrane; a protecting membrane disposed atop said optically opaque membrane; and an ion sensing membrane disposed atop said protecting membrane.

2. The chemically sensitive element of claim 1 wherein said optically opaque membrane consists of a metallic film.

3. A chemically sensitive element of the ion sensing field-effect transistor type including a semiconductor substrate having an upper surface and source, drain and channel regions defined at said upper surface; a gate insulating membrane disposed atop said channel region; a protective membrane disposed atop said gate insulating membrane; an optically opaque membrane disposed atop said protective membrane and being at least coextensive with said upper surface; and an ion sensing membrane disposed atop said optically opaque membrane.

4. The chemically sensitive element of claim 3, wherein said optically opaque member consists of a metallic film.

* * * * *